United States Patent
Marghalani

(10) Patent No.: US 11,382,727 B1
(45) Date of Patent: Jul. 12, 2022

(54) THREE-DIMENSIONAL ORAL IMAGING SYSTEM AND METHOD

(71) Applicant: Thamer Marghalani, Jeddah (SA)

(72) Inventor: Thamer Marghalani, Jeddah (SA)

(*) Notice: Subject to any disclaimer, the term of this patent is extended or adjusted under 35 U.S.C. 154(b) by 0 days.

(21) Appl. No.: 17/324,980

(22) Filed: May 19, 2021

(51) Int. Cl.
 *A61C 9/00* (2006.01)
 *A61C 1/00* (2006.01)
 *A61B 1/24* (2006.01)

(52) U.S. Cl.
 CPC .......... *A61C 9/0053* (2013.01); *A61C 1/0015* (2013.01); *A61C 9/0006* (2013.01); *A61B 1/24* (2013.01)

(58) Field of Classification Search
 CPC ... A61C 9/0053; A61C 1/0015; A61C 9/0006; A61B 1/24
 See application file for complete search history.

(56) References Cited

U.S. PATENT DOCUMENTS

| | | | | |
|---|---|---|---|---|
| 4,003,132 A | * | 1/1977 | Beck | A61C 9/0006 433/42 |
| 4,173,219 A | * | 11/1979 | Lentine | A61C 19/063 128/861 |
| 4,428,373 A | * | 1/1984 | Seid | A61C 19/063 433/80 |
| 4,902,227 A | * | 2/1990 | Smith | A61C 19/063 433/215 |
| 5,316,473 A | * | 5/1994 | Hare | A61C 19/004 433/215 |
| 5,487,662 A | | 1/1996 | Kipke et al. | |
| 5,702,250 A | | 12/1997 | Kipke | |
| 5,895,218 A | * | 4/1999 | Quinn | A61C 19/063 433/80 |
| 6,077,073 A | * | 6/2000 | Jacob | A61C 19/066 433/29 |
| 6,099,314 A | | 8/2000 | Kopelman et al. | |
| 6,386,867 B1 | | 5/2002 | Durbin et al. | |
| 6,402,707 B1 | | 6/2002 | Ernst | |
| 6,439,888 B1 | | 8/2002 | Boutoussov et al. | |
| 6,948,936 B2 | | 9/2005 | Miller et al. | |
| 6,956,601 B2 | | 10/2005 | Squilla et al. | |
| 6,976,841 B1 | * | 12/2005 | Osterwalder | A61C 19/063 433/29 |
| 7,013,191 B2 | | 3/2006 | Rubbert et al. | |
| 7,106,958 B2 | | 9/2006 | Kershbaumer et al. | |
| 7,244,122 B2 | | 7/2007 | Jung et al. | |

(Continued)

*Primary Examiner* — Nicholas D Lucchesi
(74) *Attorney, Agent, or Firm* — John A. Arsenault; Galen Peterson

(57) ABSTRACT

An oral imaging system and method for acquiring dental impression scans is provided by having one or more imaging strips with illumination elements and imaging sensors that are positioned along the contour of the various surfaces of a dental tray and acquire images of the lips, teeth, and gum regions of a mouth. Fluid channels interconnecting a vacuum source or pressurized air source to openings near the imaging sensors on the dental tray are provided to reduce condensation on the imaging sensors. An extraoral extension may also be provided to acquire images of the exterior region of the lips. Furthermore, two dental trays of the present invention may be stacked together so that the entire mouth may be scanned at one time. A ramp is provided on the lower dental tray in the stacked configuration for acquiring relative jaw positions.

18 Claims, 9 Drawing Sheets

(56) References Cited

U.S. PATENT DOCUMENTS

| | | |
|---|---|---|
| 7,312,924 B2 | 12/2007 | Trissel |
| 7,361,020 B2 | 4/2008 | Abolfathi et al. |
| 7,545,372 B2 | 6/2009 | Kopelman et al. |
| 7,572,124 B2 | 8/2009 | Cipolla |
| 8,029,278 B1 * | 10/2011 | Levine ............... A61C 19/066 433/29 |
| 8,184,147 B2 | 5/2012 | Crucs et al. |
| 8,366,442 B2 | 2/2013 | Schmitt |
| 8,591,227 B2 | 11/2013 | Levine |
| 8,831,528 B2 | 9/2014 | Shi |
| 8,971,999 B2 | 3/2015 | Kim |
| 8,989,567 B1 * | 3/2015 | Pulido ................. A61B 1/24 396/16 |
| 9,131,909 B1 * | 9/2015 | Ganz .................... A61B 6/04 |
| 9,226,801 B2 | 1/2016 | Groscurth et al. |
| 9,763,760 B2 * | 9/2017 | Senn ................... G01N 21/55 |
| 10,206,757 B2 | 2/2019 | Pettersson |
| 10,213,275 B2 | 2/2019 | Groscurth et al. |
| 11,064,957 B2 * | 7/2021 | Martin ................. A61B 5/682 |
| 2002/0055082 A1 * | 5/2002 | Durbin ................ G06T 17/00 433/29 |
| 2003/0143512 A1 | 7/2003 | Hirsch et al. |
| 2005/0084816 A1 * | 4/2005 | Mehdizadeh ........... A61B 1/24 433/29 |
| 2005/0202363 A1 | 9/2005 | Osterwalder |
| 2008/0032252 A1 | 2/2008 | Hayman et al. |
| 2010/0067756 A1 | 3/2010 | Hart et al. |
| 2010/0260405 A1 | 10/2010 | Cinader, Jr. |
| 2011/0076636 A1 * | 3/2011 | Wolff ................. A61C 19/066 433/27 |
| 2011/0207074 A1 | 8/2011 | Hall-Holt et al. |
| 2011/0217667 A1 | 9/2011 | Groscurth et al. |
| 2012/0064477 A1 | 3/2012 | Schmitt |
| 2013/0027516 A1 | 1/2013 | Hart et al. |
| 2014/0132747 A1 | 5/2014 | Andrews |
| 2014/0248576 A1 | 9/2014 | Tchouprakov et al. |
| 2014/0277665 A1 * | 9/2014 | Fisker ................... G06F 30/00 700/98 |
| 2014/0345626 A1 * | 11/2014 | Brett ................. A63B 71/085 128/861 |
| 2015/0056575 A1 | 2/2015 | Groscurth et al. |
| 2015/0079534 A1 * | 3/2015 | Tsuji .................... A61C 9/006 433/29 |
| 2015/0118638 A1 | 4/2015 | Cowburn |
| 2015/0164618 A1 * | 6/2015 | Heacock ............... A61C 7/08 433/6 |
| 2016/0014396 A1 | 1/2016 | Glinec et al. |
| 2016/0242692 A1 * | 8/2016 | McAuliffe ........... G06F 30/00 |
| 2016/0262856 A1 * | 9/2016 | Atiya ................... A61B 1/015 |
| 2017/0049607 A1 * | 2/2017 | Thornton ............. A61F 5/566 |
| 2017/0215997 A1 * | 8/2017 | Martin ................ A61B 5/6844 |
| 2017/0231733 A1 | 8/2017 | Schmid et al. |
| 2018/0000563 A1 * | 1/2018 | Shanjani ............... A61B 5/682 |
| 2018/0140394 A1 | 5/2018 | Atiya et al. |
| 2019/0365237 A1 * | 12/2019 | Lee ................... A61B 1/00045 |
| 2020/0230432 A1 * | 7/2020 | Jablow ............... A61C 17/22 |
| 2020/0360118 A1 * | 11/2020 | Olivier ................ A61B 1/24 |
| 2021/0059534 A1 * | 3/2021 | Okiyama ........... A61B 1/00135 |
| 2021/0127979 A1 * | 5/2021 | Binkowski .......... A61B 5/0088 |

* cited by examiner

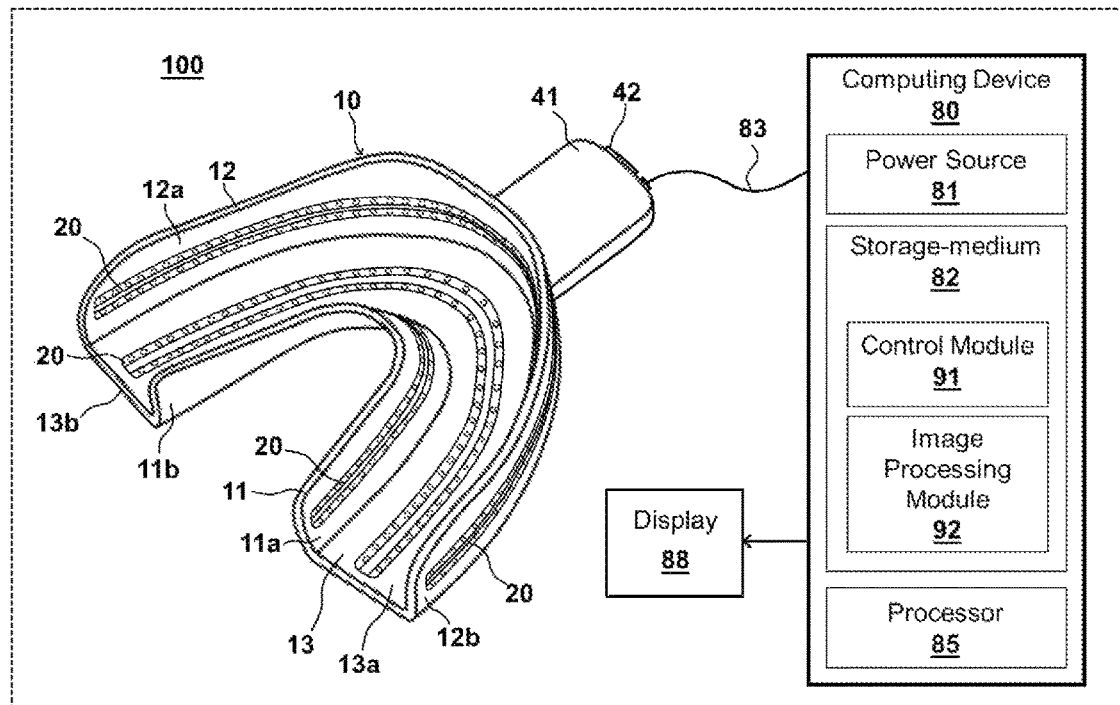
FIG. 1A
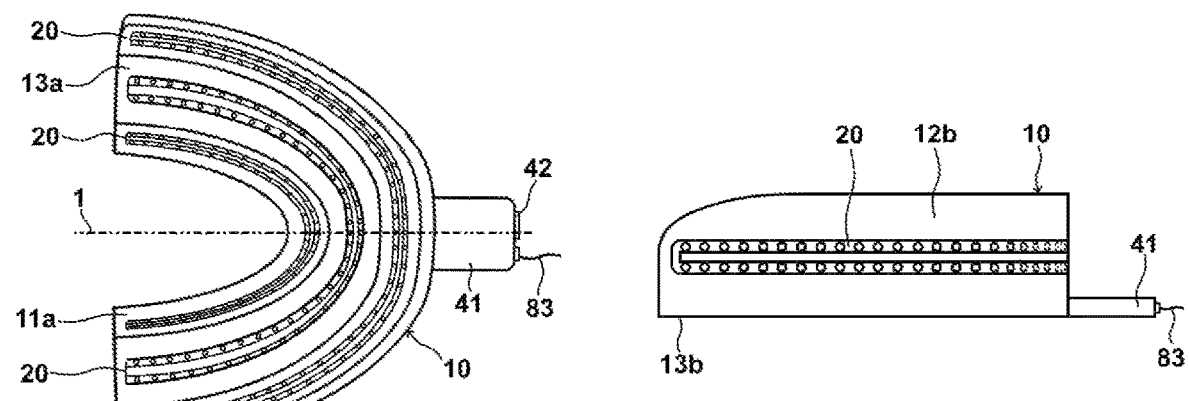
FIG. 1B
FIG. 1C

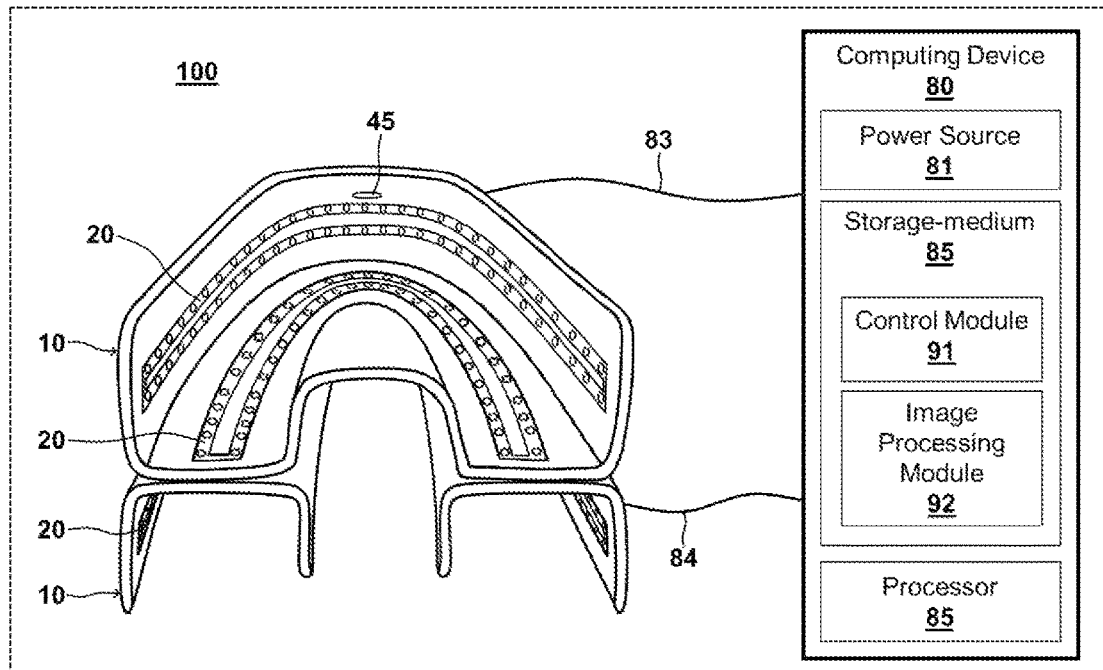
FIG. 5A
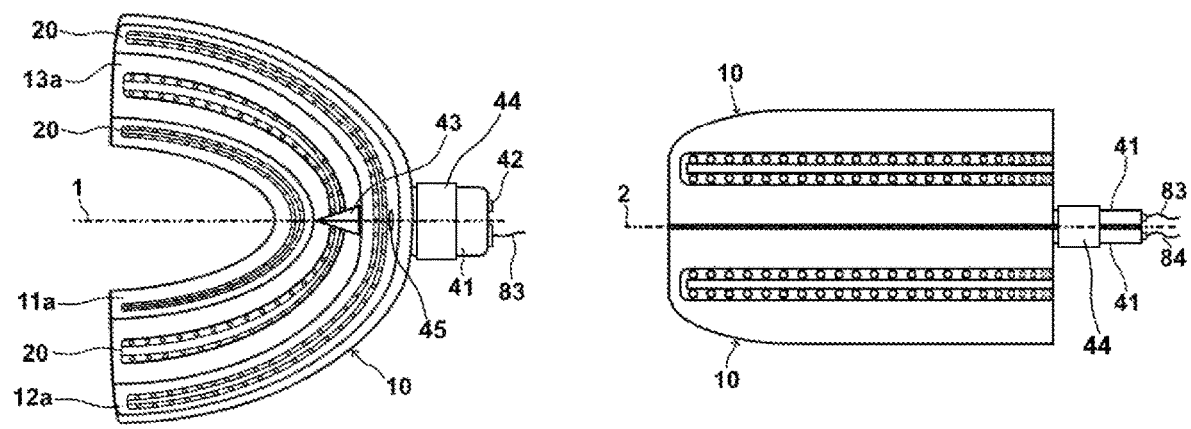
FIG. 5B
FIG. 5C

THREE-DIMENSIONAL ORAL IMAGING SYSTEM AND METHOD

STATEMENT REGARDING FEDERALLY SPONSORED RESEARCH AND DEVELOPMENT

Not Applicable.

FIELD OF INVENTION

Embodiments of the present invention relate to the field of oral scanning, and relate more specifically to a system and method for using a dental tray device for intraoral and extraoral scanning.

BACKGROUND OF DISCLOSURE

Numerous processes for acquiring dental impressions have been implemented for the purpose of creating comfortably-fitting, functional, and cosmetically appealing dental restorations. Information acquired by such processes are typically used for careful planning of dental surgeries as well as for gaining a better understanding of orthodontic movements. Analog techniques typically involve taking an impression using an elastic material; however, these techniques bear the disadvantages of increased discomfort to the user and increased procedure time. Digital intraoral scanning (IOS) techniques offer many benefits over traditional, analog techniques, including the ability to acquire three-dimensional (3D) digital impressions with a higher degree of accuracy, greater strength and comfort to the user. The 3D digital impressions can then be manufactured through reverse engineering procedures by means of computer-aided design (CAD) and computer assisted manufacturing (CAM) systems.

Two common types of digital IOS devices that have been implemented are scanner wands and benchtop scanners. Scanner wands offer a compact and light-weight method for acquiring 3D images but with many inherent disadvantages, such as errors in the resulting 3D images due to movement between the source and target, or discomfort to the person being scanned. Benchtop scanners are a bulky alternative to scanner wands and typically consist of two cameras or sensors attached to a rotating mechanism where the objects being scanned are rotated on several axes so that the scanner can accurately capture details from several perspectives. Several alternative intraoral devices have been described that attempt to overcome the issues presented by scanner wands and benchtop scanners. These devices, however, frequently exhibit other notable problems, such as difficulty in detecting deep margin lines in prepared teeth or in the case of bleeding, problems arising from condensation of water on the lenses. There exists a need for a lightweight, compact digital IOS device and method capable of acquiring high resolution 3D images of the teeth, lips, and gums in a timely manner and with minimal discomfort.

SUMMARY OF THE DISCLOSURE

The present invention provides an oral imaging system and method for scanning the interior and exterior regions of a mouth. In a preferred embodiment, the oral imaging system comprises a dental tray having one or more imaging strips positioned on the various surfaces of the dental tray. Each imaging strip has an illumination strip extending along the length of the imaging strip for providing light to the region of the mouth being scanned. Each imaging strip is also equipped with one or more imaging sensors for acquiring images of the region of the mouth being scanned, each imaging sensor being positioned in proximity to and along the illumination strip in a configuration that may be either expanded or condensed and may be either matched or alternating. In matched configurations, the imaging sensors are positioned on both sides of a respective illumination strip and directly across from one another. In alternating configurations, the imaging sensors are positioned on both sides of a respective illumination strip diagonally across from one another.

It is a feature of the present invention that suction channels or blow channels positioned in proximity to the imaging sensors along the edge of the imaging strip significantly reduce the amount of water that condenses on or stays condensed on the imaging sensors while the dental tray is inside a mouth.

It is a feature of the present invention to integrate technology such as time of flight cameras, one or more polarizing lenses for imaging sensors used herein, or similar functionality to reduce the need for powders that reduce the reflectivity of teeth when taking a dental impression.

It is a feature of the present invention that an extraoral extension be reversibly attachable to the handle of the dental tray so that the exterior regions of the lips may also be scanned at the same time as the interior regions of the mouth.

It is a feature of the present invention that two embodied dental trays may be used in a stacked configuration to scan the entire oral region of a user at one time. It is a further feature of the present invention that for embodiments having two dental trays in a stacked configuration, a detachable triangular ramp placed in the fitting surface of the lower, or mandibular tray compartment allows for the efficient and effective placement, positioning, and directing of the lower jaw and associated condyles toward the Centric Relation (CR), a repeatable and reliable position used in recording the jaw relations. Furthermore, it is a feature of the present invention that excursive movement data may be acquired by placing accelerometers or other relational data sensors on the dental trays and any teeth, gums, or dental structures, moving the lower jaw in opening and closing and to left and right relative to the initial jaw position, capturing multiple images, and comparing relational data.

It is a feature of the present invention that, during operation of the oral imaging system, the position and orientation of the imaging sensors and illumination strips are substantially stationary with respect to the oral features being imaged through lens based optical imaging stabilization, thus allowing for improved image capture over wand and other non-stationary type devices.

It is a feature of the present invention that the imaging strips contemplated herein are manufactured using flexible printed circuit boards to allow the imaging strips to curve along and conform to the U-shape of a mouth. The inventor contemplates manufacturing the flexible printed circuit boards of an imaging strip to comprise a thin insulating polymer film having conductive circuit patterns affixed thereto and supplied with a thin polymer coating to protect the conductor circuits, in addition to the power source connection to the tray itself to provide energy to the sensors and lenses along the strip needed to take a digital impression.

It is a feature of the present invention to acquire digital dental impression data with high accuracy and reduced scanning time while also reducing patient discomfort. The present invention is capable of utilizing a variety of image processing techniques, is energy efficient, and exhibits a high degree of reusability, all of which can contribute to an overall reduced cost for manufacturing a physical model of the dental impression.

It is a feature of the present invention to utilize the images and digital dental impression data and transform them into a visual representation on a display and provide a sufficient set of data to provide a three-dimensional representation of the patient's upper or lower teeth as well as information about a patient's jaw.

Embodiments include one, more, or any combination of all of the features listed above. Other features and advantages of the present invention will become apparent from the following more detailed description, taken in conjunction with the accompanying drawings, which illustrate, by way of example, the principles of the invention.

DESCRIPTION OF THE DRAWINGS

FIG. 1A is an upper perspective view of an oral imaging system, in accordance with an exemplary embodiment of the present invention;

FIG. 1B illustrates a top view of the dental tray shown in FIG. 1A, in accordance with an exemplary embodiment of the present invention;

FIG. 1C illustrates a side view of the dental tray shown in FIG. 1A, in accordance with an exemplary embodiment of the present invention;

FIG. 5A is an upper perspective view of an alternative oral imaging system, wherein the system is in a stacked configuration, and the lower dental tray incorporates a ramp, in accordance with an exemplary embodiment of the present invention;

FIG. 5B illustrates a bottom view of the lower dental tray of FIG. 5A, in accordance with an exemplary embodiment of the present invention;

FIG. 5C illustrates a side view of the dental trays shown in FIG. 5A, in accordance with an exemplary embodiment of the present invention;

DETAILED DESCRIPTION OF THE DISCLOSED EMBODIMENT

Figure 2A:
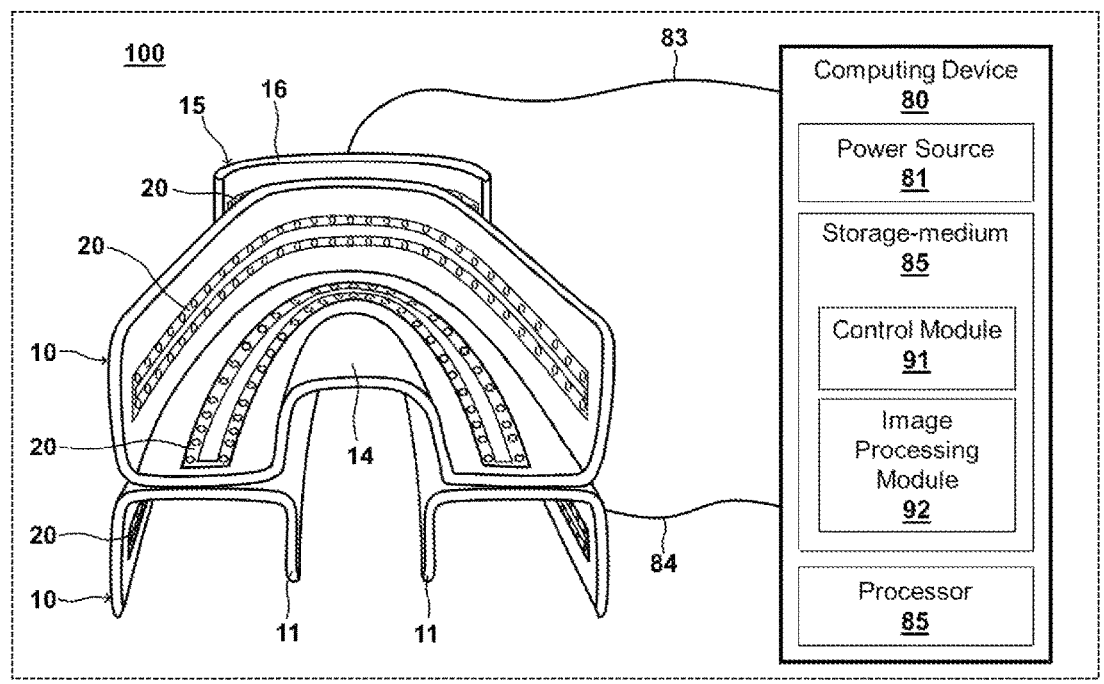
FIG. 2A is an upper perspective view of an alternative oral imaging system, wherein the system is in a stacked configuration and each dental tray incorporates an extraoral extension, in accordance with an exemplary embodiment of the present invention.

Illustrative embodiments of the invention are described below in the accompanying Figures. The following detailed description provides detailed schematics for a thorough understanding of and an enabling description for these embodiments. One having ordinary skill in the art will understand that the invention may be practiced without certain details. In other instances, well-known structures and functions have not been shown or described in detail to avoid unnecessarily obscuring the description of the embodiments. In the description, terms such as "upper", "lower", "top", "bottom", "inner", and "outer" should be construed to refer to orientation as then described or as shown in the drawings under discussion. The terms are for convenience of description and do not require that the system or component of the system be operated in a particular orientation.

FIG. 1A is an upper perspective view of an oral imaging system 100, in accordance with an exemplary embodiment of the present invention. FIG. 1B illustrates a top view of the dental tray 10 shown in FIG. 1A, in accordance with an exemplary embodiment of the present invention. FIG. 1C illustrates a side view of the dental tray 10 shown in FIG. 1A, in accordance with an exemplary embodiment of the present invention. The oral imaging system 100 may comprise a dental tray 10 equipped with one or more imaging strips 20, a handle 41 extending therefrom the dental tray 10, and a first communication link 83 between the dental tray 10 and a computing device 80. The dental trays 10 for the lower dental region and the upper dental region are each defined by a generally U-shaped channel formed to at least partially surround the teeth and gums of a patient, whereby the U-shaped channel may comprise an inner wall 11 having inner internal surface 11a and inner external surface 11b, an outer wall 12 having outer internal surface 12a and outer external surface 12b, and a base 13 interconnecting the inner wall 11 and the outer wall 12 and having a base internal surface 13a and a base external surface 13b.

The imaging strips 20 may be adhered directly to or incorporated within any one or more of internal surfaces 11a, 12a, or 13a, or outer external surface 12b, and each imaging strip 20 is generally length-wise oriented parallel with the curvature of a corresponding internal surface 11a, 12a, 13a, or 12b. The computing device 80 may comprise a power source 81, a computer-readable storage medium 82, and a processor 85, wherein the storage medium 82 may include a control module 91 and an image processing module 92. Printed circuit boards 25 housed within the imaging strips 20 or within the body of the dental tray 10 transmit or receive electrical or imaging signals between the imaging strips 20 and the computing device 80 via first communication link 83, which may be a transmission cable or wireless transmitter and receiver. Images and other information acquired or generated by the imaging system 100 may be communicated to a visual display 88 for viewing. The power source 81 provides power to components of the dental tray and/or the computing device 80.

Figure 2B:
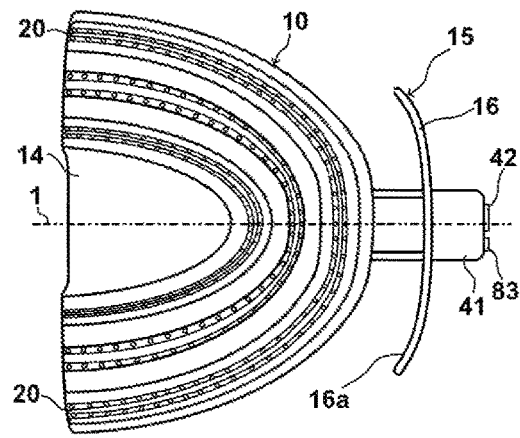
FIG. 2B illustrates a top view of the dental trays shown in FIG. 2A, in accordance with an exemplary embodiment of the present invention.
Figure 2C:
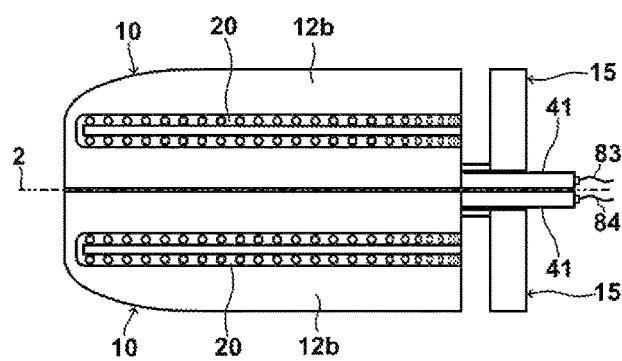
FIG. 2C illustrates a side view of the dental trays shown in FIG. 2A, in accordance with an exemplary embodiment of the present invention.
Figure 2D:
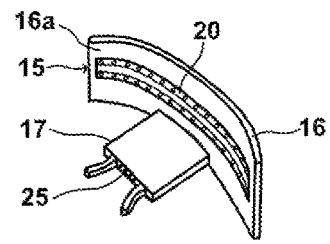
FIG. 2D illustrates a perspective view of an extraoral attachment, in accordance with an exemplary embodiment of the present invention.
Figure 2E:
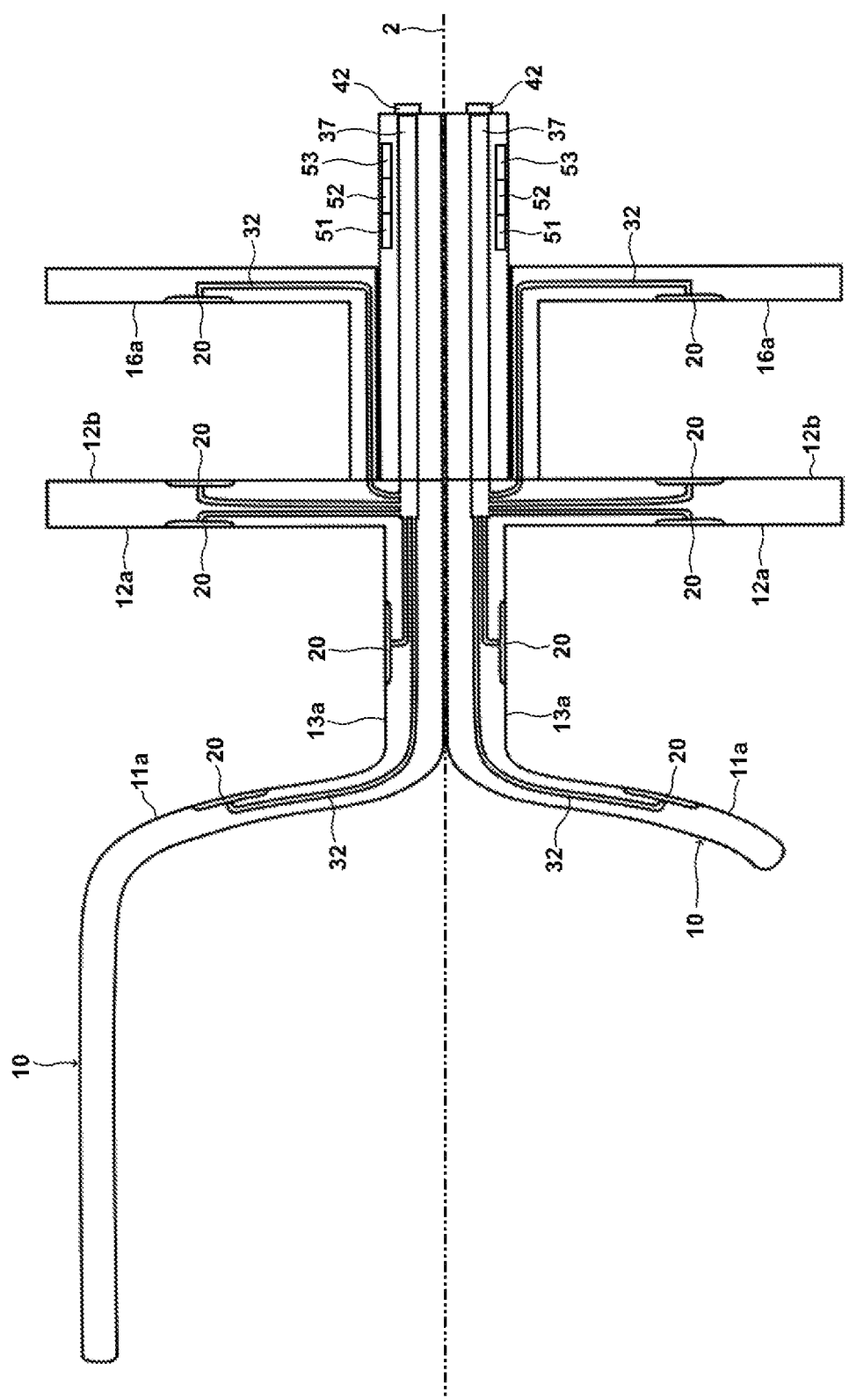
FIG. 2E illustrates a side cross-sectional view at the first longitudinal center plane of the dental trays shown in FIGS. 2A-2C, in accordance with an exemplary embodiment of the present invention.

FIG. 2A is an upper perspective view of an alternative oral imaging system 100, wherein the system 100 is in a stacked configuration and each dental tray 10 incorporates an extraoral extension 15, in accordance with an exemplary embodiment of the present invention. FIG. 2B illustrates a top view of the dental trays 10 shown in FIG. 2A, in accordance with an exemplary embodiment of the present invention. FIG. 2C illustrates a side view of the dental trays 10 shown in FIG. 2A, in accordance with an exemplary embodiment of the present invention. FIG. 2D illustrates a perspective view of an extraoral attachment 15, in accordance with an exemplary embodiment of the present invention. FIG. 2E illustrates a side cross-sectional view at the first longitudinal center plane 1 of the dental trays 10 shown in FIGS. 2A-2C, in accordance with an exemplary embodiment of the present invention.

In this example embodiment, two dental trays 10 are in a stacked configuration with the base external surface 13b of the upper dental tray 10 positioned adjacent to a base external surface 13b of the lower dental tray 10 about a second longitudinal center plane 2, each dental tray 10 having an extraoral extension 15 so that both the upper, lower, internal and external sections of a mouth may be scanned and imaged simultaneously. The extraoral extensions 15 reversibly fasten to the dental trays 10 proximate to the handles 41 if scanning of the mouth exterior is desired by the user. An extraoral extension 15 may comprise an extraoral elongation 16, a clipping member 17, and one or more imaging strips 20. The clipping member 17 inserts into a receiving member positioned within the volume of each dental tray 10 proximate to the respective handle 41. The extraoral elongation 16 has an extension internal surface 16a and is designed to be positioned closely against the lips or the extraoral region of a user by curving towards a respective dental tray 10 with increasing distance from the first longitudinal center plane 1. The dental tray 10 for the upper dental region may further comprise a central inner platform 14 connecting the two opposing sides of the inner wall 11.

In this example embodiment, additional imaging strips 20 may be adhered directly to or incorporated within any one or more of surfaces 12b or 16a, and each imaging strip 20 is generally length-wise oriented parallel with the curvature of a corresponding surface of either 12b or 16a or within the palatal section of the dental tray 10. Each type of imaging strip 20 is manufactured to substantially match the contour of a corresponding surface 11a, 12a, 12b, 13a or 16a. An imaging strip 20 may be securely fastened to the inner internal surface 11a for generating oral images of the inner gums and inner side of the teeth or inner oral structures. An imaging strip 20 may be securely fastened to the outer internal surface 12a for generating oral images of the outer side of teeth and outer gums or outer oral structures. An imaging strip 20 may be securely fastened to the base internal surface 13a for generating oral images of the teeth crowns and lower gums or lower oral structures. An imaging strip 20 may be securely fastened to the outer external surface 12b for generating oral images of the inner side of the lips. An imaging strip 20 may be securely fastened to the extension internal surface 16a for generating oral images of the outer side of the lips.

Furthermore, the oral imaging system 100 may further comprise a second communication link 84 between the computing device 80 and the second dental tray 10 for transmitting or receiving electrical or imaging signals between the imaging strips 20 on the second dental tray 10 and the computing device 80.

In some embodiments, any of the dental trays 10 may further comprise an internal power source 51, an internal memory 52, or an internal processor 53. It is contemplated that internal power source 51 may include a button cell battery located on or within the handle 41 of a dental tray 10, a rechargeable battery powered by an induction coil located on the outside surface of the handle 41 or within the handle 41 of a dental tray 10 that may be placed into sufficient physical contact with another induction coil on a flat surface of a charging base station, a rechargeable the dental tray 10 that are placed into sufficient physical contact with charging connection pins on a charging base station wherein the dental tray may be securely stored during the charging process, or a rechargeable battery that may be connected to an external power source via a cable to recharge. A millimeter wave wireless receiver placed in the handle 41 of the dental tray 10 may be wirelessly powered via a base station broadcasting a compatible signal to send wireless power to a receiver in the handle 41. Use of induction based wireless charging herein is contemplated because there would be a smaller area wherein moisture could accumulate within the interior portions of the tray 10. In addition to a charging station, a contemplated base station may also include a means to sterilize a dental tray 10 via one or more ultraviolet lights lights placed above and around the dental tray 10 or through activating a haptic chip at or near the surface of the charging station wherein cavitation and implosion is achieved via ultrasonic agitation of a fluid or solvent within a charging station. Internal memory 52 may be a solid state drive or other computer-readable storage medium capable of storing information from the illumination strips 20 prior to transmitting signals to the computing device 80. Internal processor 53 may be configured to process various forms of data between the computing device 80 and the internal memory 52.

Figure 3A:
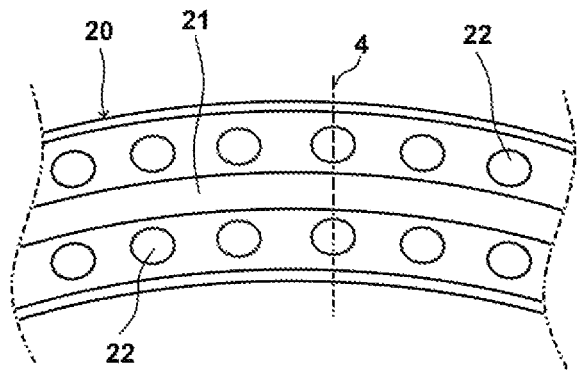
FIG. 3A illustrates a close-up top view of a section of an imaging strip in a condensed matched configuration, in accordance with an exemplary embodiment of the present invention.
Figure 3B:
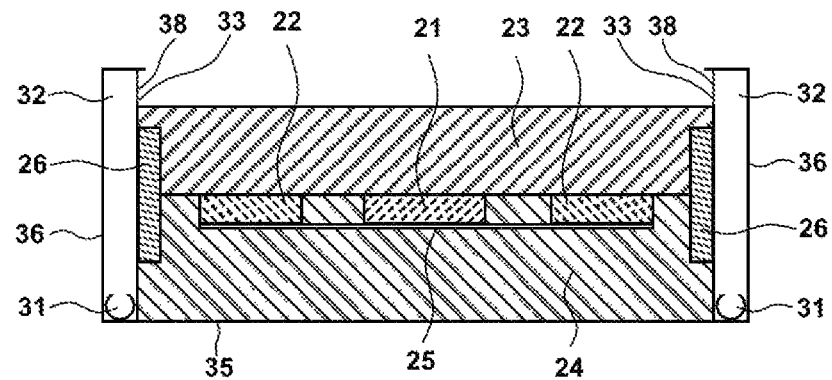
FIG. 3B illustrates a cross-sectional view of a section of the imaging strip shown in FIG. 3A, in accordance with an exemplary embodiment of the present invention.

FIG. 3A illustrates a close-up top view of a section of an imaging strip 20 in a condensed matched configuration, in accordance with an exemplary embodiment of the present invention. FIG. 3B illustrates a cross-sectional view of a section 4 of the imaging strip 20 shown in FIG. 3A, in accordance with an exemplary embodiment of the present invention. Each imaging strip 20 may comprise one or more illumination strips 21 and a plurality of imaging sensors 22 along the imaging strip 20 as an array. The illumination strips 21 may comprise a plurality of adjacently positioned individual light sources or may be a single continuous illuminating extension. The illumination strips 21 are configured to provide illumination to the region of the mouth being imaged and are generally either light emitting diodes (LED), structured striped light, lasers, infrared sources, other coherent light sources, or combinations thereof. The imaging sensors 22 are configured to acquire images of the teeth and gum regions of the mouth and transmit the acquired images to the computing device 80 via printed circuit boards 25 and communication links 83 and 84. A variety of imaging sensors 22 may be used including, but not limited to, optical imaging sensors, time of flight sensors, laser sensors, blue CAM sensors, back-illuminated CMOS, three-dimensional cameras, optical coherence tomography (OCT), other various types of optical camera sensors, or combinations thereof. The imaging sensors 22 may also include lens-based optical imaging stabilization for more accurate imaging via an internal floating lens element within the sensor, wherein the floating lens is electronically controlled and shifts the lens opposite to the direction a lens is moved. The inventor contemplates using one or more wide-angle imaging sensors along the imaging strip in order to capture a plurality of close-up images which may then be transformed for sharpness and then consolidated into a single three-dimensional impression image via imaging software that may then be output to a display. Furthermore, it is contemplated that the imaging system 100 could be improved by including a hydrophobic coating onto the outer surface of the imaging sensors 22 for preventing fog or condensation on the surface of the sensors 22.

The illumination strips 21 and imaging sensors 22 may be directly attached between a first cover layer 23 and a second cover layer 24. The first cover layer 23 and second cover layer 24 protect the illumination strips 21 and imaging sensors 22 from damage caused by abrasion and bodily fluids and are manufactured from a polymer exhibiting a substantially high transparency and at least partial flexibility. The inventor contemplates using polyimide, polyester, or a similar polymer as a base material for a flexible printed circuit board 25 used for the imaging strip 20 and connecting the imaging strip 20 to a power source 51 or 81, illumination strips 21, imaging sensors 22, or other electronic components. The first cover layer 23 provides a minimal imaging distance between the imaging sensors 22 and the target to be imaged and exhibits a substantially high transmissivity of light. The second cover layer 24 houses the illumination strips 21, the imaging sensors 22, and printed circuit boards 25. In various embodiments, one or more of the imaging strips 20 may each comprise one or more fluid collection channels 31 extending along the back portion 35 of at least one transverse end portion 36 of the imaging strip 20 and each being designed to communicate fluid from one or more blow channels 32 to a vacuum. The fluid collection channels 31 may have either a semi-elliptical cross section or may have holes along the length of each fluid collection channel 31 and generally converge into a main fluid channel 37 located near and within the handle 41 of the dental tray 10 before terminating at a blower/vacuum line 42, or channel, that attaches to a pressurized air supply or vacuum. The blow channels 32 generally extend adjacently along the transverse end portions 36 and communicate fluid from the blow channel openings 33 to the fluid collection channels 31. In various embodiments, any imaging strip 20 with blow channels 32 may further comprise a mesh 38 for filtering particles from entering the blow channels 32, the mesh 38 generally being positioned at the blow channel openings 33. In various embodiments, the imaging strips 20 may further comprise one or more heating elements 26 for applying heat to the air and surfaces of the blow channels 32 or to the first cover layer 23 or second cover layer 24. The heating elements 26 are generally positioned adjacent to and along the blow channels 32.

Figure 4A:
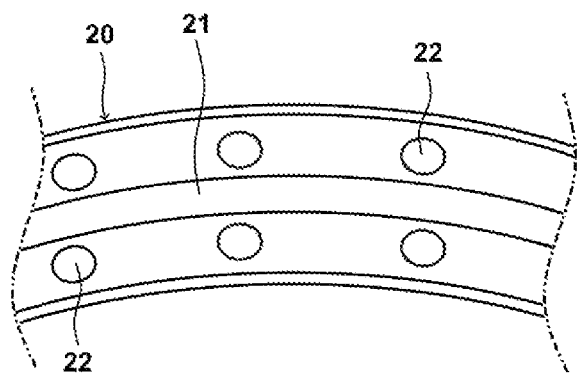
FIG. 4A illustrates a top view of an embodiment of an imaging strip for generating oral images using an expanded matched configuration, in accordance with an exemplary embodiment of the present invention.
Figure 4B:
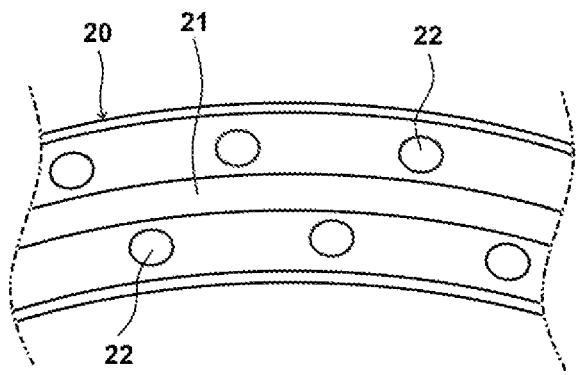
FIG. 4B illustrates a top view of an embodiment of an imaging strip for generating oral images using a condensed alternating configuration, in accordance with an exemplary embodiment of the present invention.
Figure 4C:
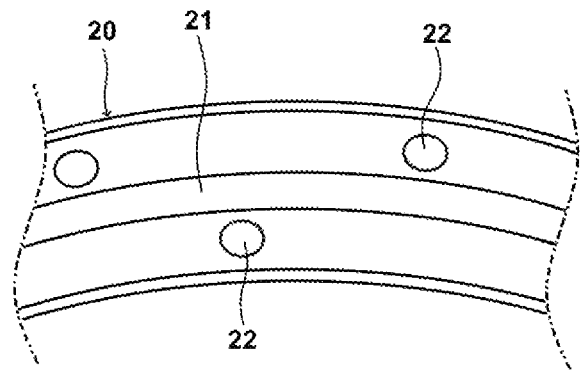
FIG. 4C illustrates a top view of an embodiment of an imaging strip for generating oral images using an expanded alternating configuration, in accordance with an exemplary embodiment of the present invention.

FIG. 4A illustrates a top view of an embodiment of an imaging strip 20 for generating oral images using an expanded matched configuration, in accordance with an exemplary embodiment of the present invention. FIG. 4B illustrates a top view of an embodiment of an imaging strip 20 for generating oral images using a condensed alternating configuration, in accordance with an exemplary embodiment of the present invention. FIG. 4C illustrates a top view of an embodiment of an imaging strip 20 for generating oral images using an expanded alternating configuration, in accordance with an exemplary embodiment of the present invention. A user may find it advantageous to use any one of the expanded matched, expanded alternating, condensed matched, or condensed alternating configurations depending on numerous factors such as, but not limiting to, mouth size or extent of thermal dissipation from the illumination strips 21.

FIG. 5A is an upper perspective view of an alternative oral imaging system 100, wherein the system 100 is in a stacked configuration and the lower dental tray 10 incorporates a ramp, in accordance with an exemplary embodiment of the present invention. FIG. 5B illustrates a bottom view of the lower dental tray 10 of FIG. 5A, in accordance with an exemplary embodiment of the present invention. FIG. 5C illustrates a side view of the dental trays shown in FIG. 5A, in accordance with an exemplary embodiment of the present invention. In embodiments where two dental trays 10 are in a stacked configuration, the oral imaging system 100 may further comprise a ramp 43 for acquiring the jaw position of a user. The ramp 43 may take the form of a triangular pyramid or a right triangular pyramid and may be positioned on the base internal surface 13a of the lower dental tray 10. The ramp 43 may be detachable and may be sloping or inclining toward the outer internal surface 12a near the cross-section 1. The ramp 43 is designed to align the mandible and maxilla of a user towards the CR position when the lower front teeth contacts and presses against the lower dental tray 10. The three-dimensional digital scanning of the jaws and recording of this position is useful in relating and positioning of the 3D scanned models of the jaws into the correct CR position. This recorded CR position is an essential record for the proper construction of simple and complex dental prostheses and mouth rehabilitation of the patients. A clip 44 may be attached to the handles 41 of stacked dental trays 10 to firmly press the dental trays 10 together and maintain the relative positions and alignment of the dental trays 10. Other suitable methods of maintaining the relative positions and alignment of dental trays 10 in a stacked configuration include, but are not limited to, rails and respective rail inserts positioned on the base external surface 13b of each dental tray 10, adhesive materials applied to the base external surface 13b of one or more dental trays 10, or manufacturing the dental trays 10 together as a single piece. In various embodiments, one or more dental trays 10 may further comprise one or more accelerometers 45 on one of the surfaces 11a, 12a, or 13a, or directly on the imaging strip 20, as well as on any teeth, gums, or dental structures.

Figure 6:
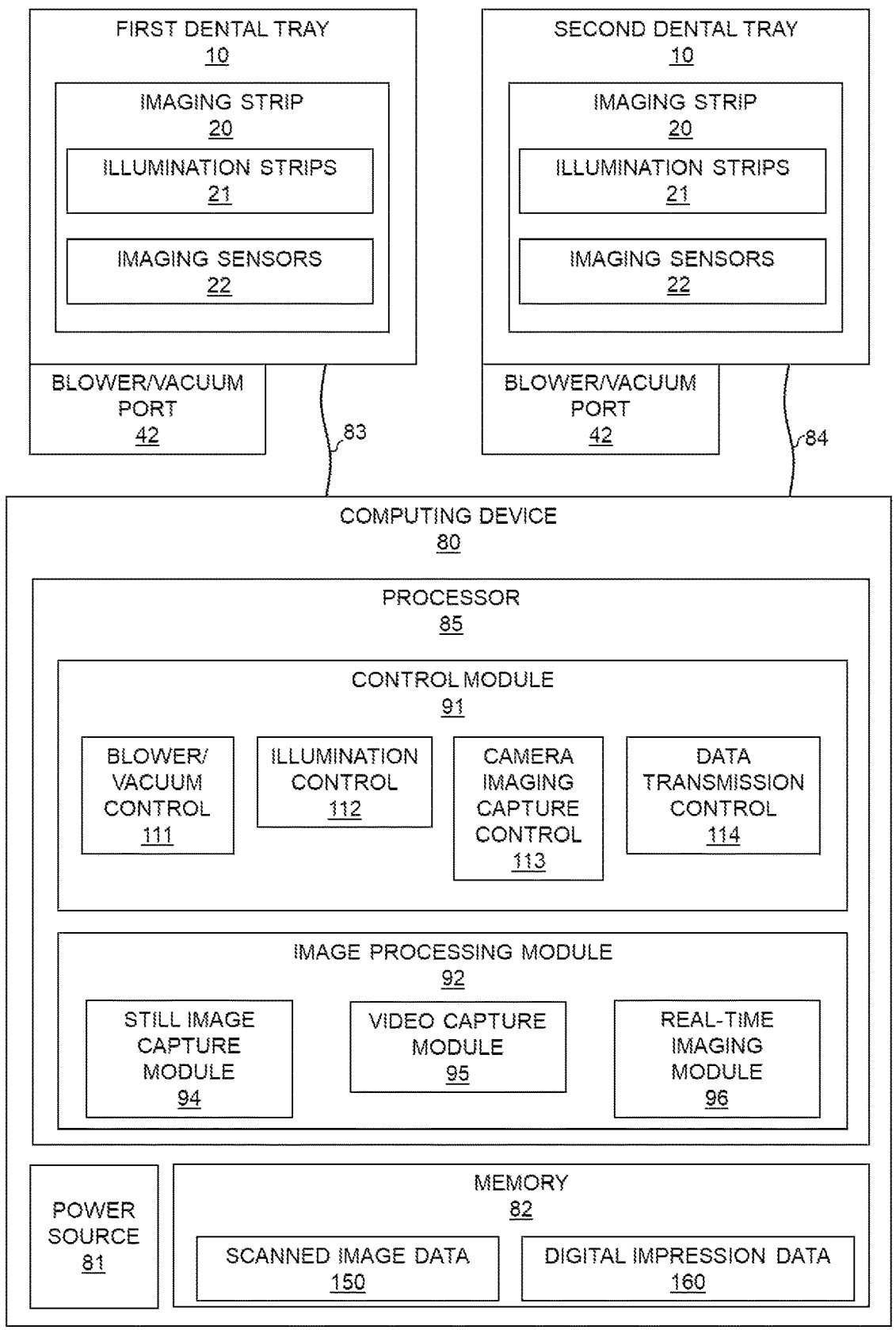
FIG. 6 illustrates a flow chart of one embodiment of the oral imaging system consistent with embodiments of the present disclosure.

FIG. 6 illustrates a flow chart of one embodiment of the oral imaging system 100 consistent with embodiments of the present disclosure. The processor 85 may be configured to perform operations, tasks or actions related to obtaining images using the imaging strips 20 on the dental tray 10 or to further process the images obtained by scanning the teeth and gum regions into digital dental impressions. The computer-readable storage medium 82 may comprise modules, software and algorithms that the processor 85 implements during the steps of the image acquisition method 200. In the embodiments described herein, representative data may refer to tabulated data, graphical data, visual data or functional relationships.

The control module 91 may comprise a blower/vacuum control 111 for controlling and adjusting the humidity and degree of either reduced or elevated pressure in the fluid collection channels 31, an illumination control 112 for controlling and adjusting the degree of illumination for the illumination strips 21, a camera imaging capture control 113 for controlling and adjusting the capture timing or rate of the imaging sensors 22, and a data transmission control 114 for controlling and adjusting the transmission of images and representative data from the dental tray(s) 10 to the computing device 80.

The image processing module 92 may comprise instructions, tasks or executable commands related to the processing of scanned images or representative data into digital dental impressions. Images or representative data from the scanning step may be further processed using a variety of techniques which include, but are not limited to, color separation and rendering techniques, multiple 3D image capture techniques, position and relation techniques, techniques using artificial intelligence, gaussian smoothing techniques, image sharpening techniques, optical coherence tomography, light detection and ranging (LiDAR), and triangulation techniques. Furthermore, the image processing module 92 may comprise instructions, tasks or executable commands related to adjusting the relative positions and orientations of the maxilla dental tray and mandible dental tray when two dental trays 10 are used simultaneously.

The image processing module 92 may comprise a still image capture module 94, a video capture module 95, or a real-time imaging module 96. The still image capture module 94 uses triangulation techniques to acquire images generally by emitting light beams that intersect to identify a particular point in 3D space. For passive triangulation techniques, Equation 1 may be used to calculate the distance (d) of a target perpendicular from the plane intersecting mediums 23 and 24 from the distance (x) between the illumination strip 21 and a respective imaging sensor 22 along the plane intersecting mediums 23 and 24, the angle (α) between the target at distance (d) and the plane intersecting mediums 23 and 24 relative to the illumination strip 21, and the angle (β) between the target at distance (d) and the plane intersecting mediums 23 and 24 relative to the respective imaging sensor 22.

$$d = \frac{x}{\frac{1}{\tan(\alpha)} + \frac{1}{\tan(\beta)}} \quad \text{(Equation 1)}$$

Furthermore, for embodiments wherein the imaging sensors 22 are fixed focus cameras, the blur ψ or defocus of generated images may be quantified by Equation 2, where λ is the wavelength of light coming from the illumination strips 21, r is a measure of the aperture of the imaging sensor 22, and $z_o^f$ and $z_o'^f$ are the in-focus and actual object distances from the imaging sensor 22.

$$\psi = \frac{2\pi}{\lambda}\left(\frac{1}{z_o^f} - \frac{1}{z_o'^f}\right)r^2 \quad \text{(Equation 2)}$$

The video capture module 95 uses active wavefront sampling techniques to acquire images by emitting blue wavelength light directed at the teeth, gums or dental structures that is detected by each individual imaging sensor 22 at different angles. The captured video images may then be then assembled or stitched together into a 3D rendering using a variety of well established techniques. The real-time imaging module 96 uses ultrafast optical sectioning techniques that generate 3D images based on real-time geometric representative data.

Figure 7:
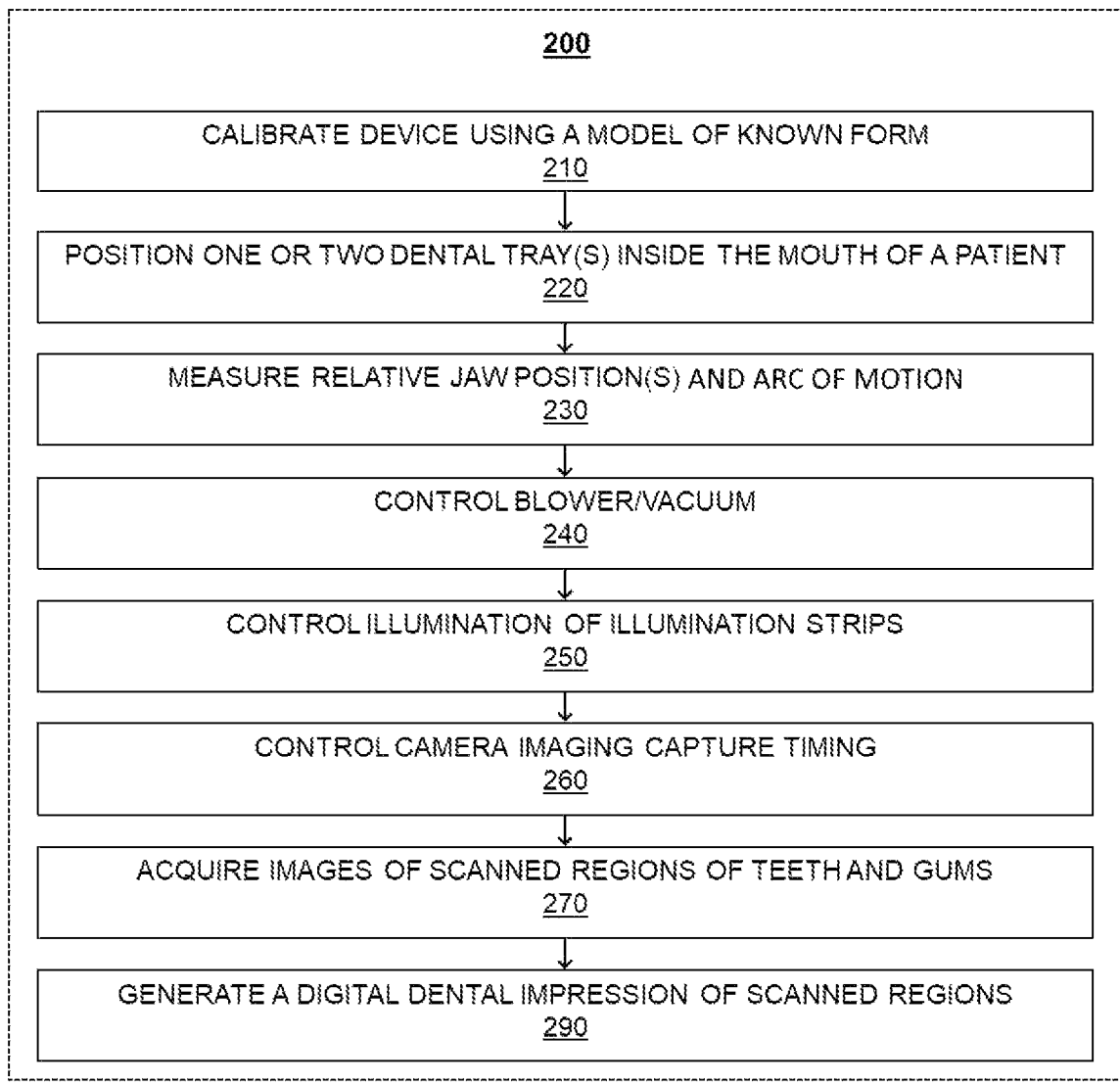
FIG. 7 illustrates a flow chart of one embodiment of the image acquisition method consistent with embodiments of the present disclosure.

FIG. 7 illustrates a flow chart of one embodiment of the image acquisition method 200 consistent with embodiments of the present disclosure. During use and operation of the oral imaging system 100, steps from the image acquisition method 200 may be implemented to acquire digital dental impressions of a user's teeth and gums as well as extraoral features of the mouth and lips. The image acquisition method 200 may comprise one or more calibration steps 210, wherein the calibration steps 210 may include the step of scanning a manufactured model of teeth and gums and adjusting parameters of the scanned image data 150 to be set substantially equal to the calibrated model. The image acquisition method 200 may comprise one or more device placement steps (Block 220), which generally involves insertion of the embodied device into the mouth of a user. In embodiments wherein two dental trays 10 are in a stacked configuration, the image acquisition method 200 may further comprise the step of a measuring relative bite or jaw positions (Block 230) and the envelope of motion, the former of which is generally performed by having the user bite the dental trays 10 together, the latter of which is generally performed by having the user move the bottom jaw up, down, left, right, and diagonal within the dental tray 10 relative to the initial jaw position and comparing with the initial jaw position data. The image acquisition method 200 may comprise the step of controlling the degree of suction or blow and affecting the humidity levels proximate to the illumination strips 21 and the imaging sensors 22 (Block 240).

The image acquisition method 200 may comprise one or more steps of controlling the extent of and the timing of illumination of one or more illumination strips 21 (Block 250). The image acquisition method 200 may comprise one or more steps of controlling the camera imaging capture timing of imaging sensors 22 (Block 260).

The image acquisition method 200 may comprise one or more image acquisition steps 270 for acquiring scanned image data 150 of the targeted areas of the patient's teeth and/or gums. During the image acquisition steps 270 of the embodied device 100, the position and orientation of the oral imaging system 100 is substantially stationary with respect to the oral features being imaged at a given time.

The image acquisition method 200 may comprise one or more steps for generating digital dental impression data 160 using the scanned image data 150 and one or more of a variety of image processing techniques (Block 290). The 3D digital impression data 160 may then be used by suitable CAD and CAM software to generate a model for the teeth and gums of a user.

Figure 8:
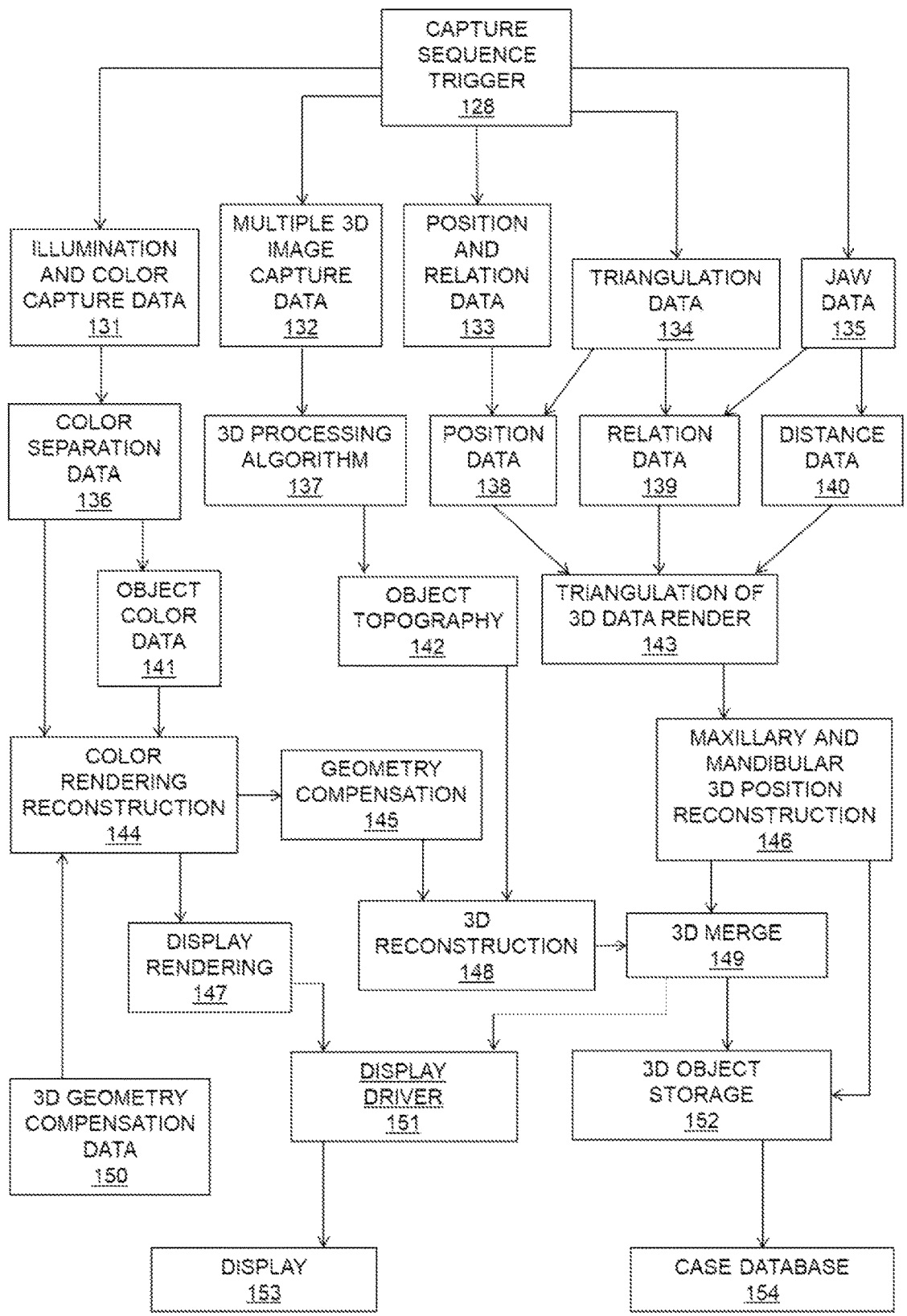
FIG. 8 illustrates a flow chart of one embodiment of the image processing module consistent with embodiments of the present disclosure.

FIG. 8 illustrates a flow chart of one embodiment of the image processing module 130 consistent with embodiments of the present disclosure. The capture sequence trigger 128 may initiate the image processing module 130 at the user's desire and may generate any combination of illumination and color capture data 131, multiple 3D image capture data 132, position and relation data 133, triangulation data 134, or jaw data 135. Color separation data 136 may be generated from illumination and color capture data 131 and may be used to generate object color data 141 or color rendering reconstruction 144; the object color data 141 or 3D geometry compensation data 150 may also be used to generate color rendering reconstruction 144. The color rendering reconstruction 144 may be used to generate geometry compensation 145 or display rendering 147.

Multiple 3D image capture data 132 may be used to generate a 3D processing algorithm 137, which may be used to generate object topography 142 that, along with geometry compensation 145, may be used to generate a 3D reconstruction 148. Position data 138 may be generated from position and relation data 133 or triangulation data 134 and may be used to generate a triangulation of 3D data render 143. Relation data 139 generated from triangulation data 134 or jaw data 135 may also be used to generate a triangulation of 3D data render 143. The triangulation of 3D data render 143 may then be used to generate a maxillary and mandibular 3D position reconstruction 146, which may be sent to 3D object storage 152 or used in conjunction with the 3D reconstruction 148 to generate a 3D merge 149. The 3D merge 149 may be sent to 3D object storage 152 or to a display driver 151 and eventually to a display 153. Data in the 3D object storage 152 may be stored within a case database 154.

While particular embodiments of the invention have been described and disclosed in the present application, it is clear that any number of permutations, modifications, or embodiments may be made without departing from the spirit and the scope of this invention. Accordingly, it is not the inventor's intention to limit this invention in this application, except as by the claims.

Particular terminology used when describing certain features or aspects of the invention should not be taken to imply that the terminology is being redefined herein to be restricted to any specific characteristics, features, or aspects of the invention with which that terminology is associated. In general, the terms used in the claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

The above detailed description of the embodiments of the invention is not intended to be exhaustive or to limit the invention to the precise embodiment or form disclosed herein or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

In general, the terms used in the claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention under the claims.

In light of the above "Detailed Description," Inventor may make changes to the invention. While the detailed description outlines possible embodiments of the invention and discloses the best mode contemplated, no matter how detailed the above appears in text, the invention may be practiced in a myriad of ways. Thus, implementation details may vary considerably while still being encompassed by the spirit of the invention as disclosed by the inventor. As discussed herein, specific terminology used when describing certain features or aspects of the invention should not be taken to imply that the terminology is being redefined herein to be restricted to any specific characteristics, features, or aspects of the invention with which that terminology is associated.

What is claimed is:

1. An oral imaging system comprising:
    a dental tray in a form of a U-shaped channel formed to at least partially surround teeth and gums;
    one or more imaging strips, wherein each imaging strip further comprises a first cover layer and a second cover layer, each said imaging strip comprising an illumination strip and a plurality of imaging sensors, whereby one or more illumination strips or imaging sensors are directly adhered between the first cover layer and the second cover layer, the first and second cover layers are configured to protect the imaging strip; and
    a handle extending therefrom said dental tray.

2. The oral imaging system of claim 1, whereby said form of a U-shaped channel comprises:
    an inner wall with an inner internal surface;
    an outer wall with an outer internal surface and an outer external surface; and
    a base with a base internal surface and a base external surface, wherein said base interconnects said inner wall and said outer wall.

3. The oral imaging system of claim 2, wherein at least one said imaging strips is adhered directly to or incorporated within said inner internal surface, said outer internal surface, or said base internal surface.

4. The oral imaging system of claim 1, further comprising a computing device, and one or more communication links between said computing device and one or more of said dental tray, wherein said one or more communication links are configured to transmit or receive imaging signals between said one or more imaging strips and said computing device.

5. The oral imaging system of claim 4, wherein said computing device comprises a power source, a computer-readable storage medium, and a processor, wherein said storage medium comprises a control module and an image processing module.

6. The oral imaging system of claim 5, wherein said control module comprises:
    a humidity suction and blow control for controlling the humidity and degree of either reduced or elevated pressure in said one or more imaging strips;
    an illumination control for controlling a degree of illumination for each illumination strips;
    a camera imaging capture control for controlling a capture timing of said imaging sensors; and
    a data transmission control for controlling transmission of representative data.

7. The oral imaging system of claim 5, wherein said image processing module comprises:
    a still image capture module;
    a video capture module; or
    a real-time imaging module.

8. The oral imaging system of claim 4, wherein one or more said imaging sensors are configured to acquire images of teeth and gum regions and transmit said images to said computing device.

9. The oral imaging system of claim 1, wherein said one or more illumination strips comprises a plurality of adjacently positioned individual light sources or a single continuous illuminating extension.

10. The imaging system of claim 1, wherein the first cover layer is configured to have a thickness configured to provide a minimal distance between one or more imaging strips and a target.

11. The imaging system of claim 1, wherein at least one said one or more imaging strips comprises:
one or more fluid collection channels extending along a back portion of at least one transverse end portion of said one or more imaging strips;
one or more blow channels extending adjacently along said one or more transverse end portions and designed to communicate fluid from one or more blow channel openings to said fluid collection channels, wherein each fluid collection channels are designed to communicate fluid between one or more blow channels and a vacuum or pressurized air source.

12. The imaging system of claim 11, wherein at least one imaging strip comprises one or more mesh positioned at one or more blow channel openings.

13. The imaging system of claim 1, wherein said imaging sensors are configured into a condensed matched configuration, a condensed alternating configuration, an expanded matched configuration, or an expanded alternating configuration.

14. The oral imaging system of claim 1, further comprising an extraoral extension, said extraoral extension comprising an extraoral elongation with an extension internal surface having an extraoral imaging strip configured to provide extraoral imaging, whereby said extraoral elongation is designed to be positioned in close proximity to lips or an extraoral region of a user, and whereby said extraoral extension is reversibly fastenable to said handle or to said dental tray.

15. The oral imaging system of claim 14, further comprising one or more additional imaging strips adhered directly to or incorporated within said extension internal surface, whereby each said additional imaging strip is oriented length-wise parallel with a curvature of said extension internal surface.

16. An oral imaging system comprising:
a first dental tray and a second dental tray, wherein each of said first dental tray and said second dental tray comprises a form of a U-shaped channel formed to at least partially surround teeth and gums, whereby said form of a U-shaped channel comprises an inner wall with an inner internal surface and inner external surface, an outer wall with an outer internal surface and an outer external surface, and a base with a base internal surface and a base external surface, wherein said base interconnects said inner wall and said outer wall;
wherein said first dental tray and said second dental tray are arranged in a stacked configuration with a first base exterior wall external surface of said first dental tray adjacently positioned configured to be substantially parallel with a second base exterior wall external surface of said second dental tray;
one or more imaging strips on each of said first dental tray and said second dental tray, each said imaging strip comprising an illumination strip and a plurality of imaging sensors; and
wherein one of two said dental trays further comprises a ramp having a triangular pyramidal shape, wherein the ramp is positioned on said base internal surface of one of said first dental tray or said second dental tray.

17. The oral imaging system of claim 16, further comprising a rail, a rail insert; wherein the rail is positioned on the base external surface of the first tray and is configured to couple with the rail insert positioned on the base external surface of the second tray.

18. A method for scanning images of a mouth region, said method comprising the steps of:
placing one or two dental trays into a mouth of a patient;
acquiring scanned image data of one or more targeted areas of the mouth via one or more imaging sensors and illuminations strips positioned along one or more surfaces of the one or two dental trays;
calibrating an oral imaging system;
measuring relative jaw positions;
controlling a degree of suction or blow and affecting humidity levels proximate to one or more illumination strips or one or more imaging sensors;
controlling an extent of and timing of illumination of one or more illumination strips;
controlling a camera imaging capture timing of one or more imaging sensors; and
generating digital dental impression data using said scanned image data.

* * * * *